(12) United States Patent
Debrouse

(10) Patent No.: US 6,845,270 B2
(45) Date of Patent: Jan. 18, 2005

(54) APPARATUS FOR DESTROYING PATHOGEN MOLECULES USING FREQUENCIES

(75) Inventor: Joseph Debrouse, Louisa, VA (US)

(73) Assignee: Joseph W. DeBrouse, Louisa, VA (US)

( * ) Notice: Subject to any disclaimer, the term of this patent is extended or adjusted under 35 U.S.C. 154(b) by 431 days.

(21) Appl. No.: 10/150,250

(22) Filed: May 17, 2002

(65) Prior Publication Data

US 2002/0138118 A1 Sep. 26, 2002

Related U.S. Application Data

(63) Continuation-in-part of application No. 09/240,023, filed on Jan. 29, 1999, now Pat. No. 6,397,106.
(60) Provisional application No. 60/073,311, filed on Jan. 29, 1998.

(51) Int. Cl.$^7$ ................................. A61N 1/32
(52) U.S. Cl. ......................... 607/72; 600/14
(58) Field of Search ............................ 607/68, 69, 72, 607/76; 600/13, 14, 15, 386

(56) References Cited

U.S. PATENT DOCUMENTS 6,735,476 B2 * 5/2004 Mellen ........................ 607/46

* cited by examiner

Primary Examiner—Kennedy Schaetzle
(74) Attorney, Agent, or Firm—Joseph W. DeBrouse

(57) ABSTRACT

A frequency transfer system for the destruction of pathogens using a recorded medium and a transfer unit is disclosed. The recorded medium contains at least one square wave at a frequency known to affect specific pathogens. Additional mathematically congruent square waves can also be recorded on the medium for simultaneous transmission. The transfer unit contains a coil and an amplifier. The coil absorbs the magnetic flux from the electromagnetic square waves and outputs scalar square waves. The amplifier increases the voltage and reverses the wave polarities to place the greatest scalar potentials at the positive node of said output square wave. The scalar waves are transferred to the user's body through output leads and electrodes.

17 Claims, 2 Drawing Sheets

APPARATUS FOR DESTROYING PATHOGEN MOLECULES USING FREQUENCIES

RELATE BACK

This application is a continuation-in-part of U.S. patent application Ser. No. 09/240,023 filed Jan. 29, 1999 now U.S. Pat. No. 6,397,106, which was based on U.S. Provisional Application No. 60/073,311 filed Jan. 29, 1998, the contents of both of which are incorporated herein as though recited in full.

BACKGROUND OF THE INVENTION

1. Field of the Invention

An inexpensive, portable apparatus, and CDs, to enable frequencies to be played from a portable or home CD player is disclosed.

2. Brief Description of the Prior Art

It has long been known that all substances are composed of atoms, each with a vibrational frequency inherent in its composition. Just as all substances have a vibrational frequency, which maintains their integrity and composition, interference with this frequency can destroy the substances integrity. This can be seen when a singer has sufficient power in their voice to bring the frequency of the sung note to the frequency of a crystal glass, thereby breaking the glass. This physical law can also be applied to the icosahedral and helical symmetry within a cell. The amplitude of a vibrational frequency can disrupt a cell, destroying the protein bonds. Viruses and other pathogens are weakly bonded and their symmetry can be considered a torsional oscillator which can be destroyed by over driving these "oscillators" at their resonant frequency.

Once the ability to detect and measure the vibrational frequencies was discovered, the destruction of pathogens was explored. This is reflected in vast amounts of prior art and publications since the 1940s. Publications such as The Rife Way 3, Mark Simpson; Blast It, Part 2: Frequency Listings for Diseases, Disorders and Other Pesky Problems, Compilation Halal Information, Texas; and The Cure for All Diseases, Hulda R. Clark, PhD, MD, New Century Press, San Diego, Calif. (1995). The use of frequencies as a muscular therapy device is disclosed in U.S. Pat. No. 4,919,139 issued to Brodard. The device, however, consists of a computer and electrodes and requires complex programming to sequence the programmed pulses. Other patents have utilized frequencies, pulses and voltages; however, none have taken the frequency of specific pathogens, recorded the frequency, and made this treatment available in a compact, inexpensive system.

Without the ability to easily bring this technology to individuals, the full benefits are difficult to achieve. The disclosed invention makes the benefits of this technology easily accessible to the public. Additionally, the disclosure takes the relationship between the square wave created by audible sound and the subsequent cascading harmonics and converts this relationship to mathematical formulas. By making this relationship computable, subsequent identification of harmonics destructive to pathogens will be easier to define.

BRIEF DESCRIPTION OF THE DRAWINGS

The advantages of the disclosure will become more apparent when read with the specification and the drawings, wherein.

DETAILED DESCRIPTION OF THE INVENTION

Figure 1:
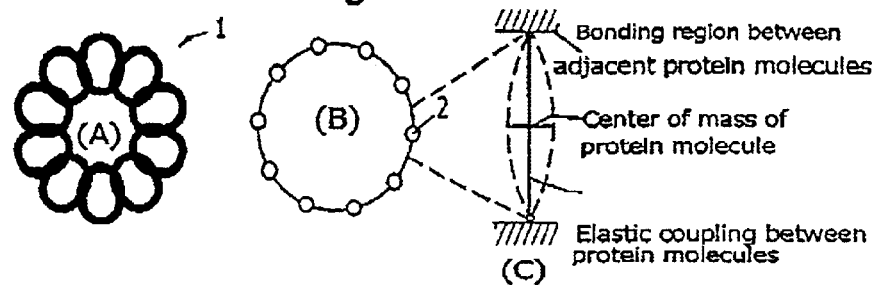
FIG. 1A shows a virus capsid protein molecule.
FIG. 1B is a mathematical abstraction of the virus.
FIG. 1C the bonding region, center of mass and elastic coupling of the protein molecule.

It is well known that all matter vibrates at a specific level. It is also known that vibrational levels can be changed through interaction with a vibration slightly higher or lower, thereby bringing the stimulated cells into forced resonance. This technique is used in meditation wherein the metronome is set for a specific brainwave cycle to lower the subject's brainwaves into a deep meditative state. The vibrational frequencies for destroying pathogenic cells were first discovered by Dr. Royal Raymond Rife. Since that time, although these frequencies were obviously known, they have not been widely used, partially due to equipment inconvenience. The equipment used by Rife, and others, was bulky and expensive, thereby requiring visits to a facility for each treatment.

The disclosed device enables this electromagnetic technology to be easily accessible to anyone having a CD player. The teachings herein enable the use of a portable CD player, as well as a station unit, and the references hereinafter are directed to the portable unit. Although the frequencies for use with the transfer unit disclosed herein can be recorded on any high quality and distortion free recording medium, such as computer chip, tape, etc., for ease of description, reference will be made herein to the use of a CD. Since the frequencies being used to break the pathogen bonds are modulated for a specific pathogen, the frequency output must be within 20% of the targeted frequency, requiring a high quality medium.

The disclosed technology has gone beyond the known and proven scientific data by amplifying the odd harmonics that naturally occur within the square wave. A sine wave can be somewhat irregular, however it is the most common waveform occurring in nature, producing even and odd harmonics, which are multiple frequencies of the fundamental. Therefore a 100 cycle per second sine wave produces harmonics of 200, 300, 400, 500, etc., cycles per second. The 100 cycles per second square wave, however produces only odd harmonics, 300, 500, 700 cycles per second and up.

It is the odd harmonics generated from a square wave that induce resonance in a body causing cells to sympathetically vibrate at the same, or nearly the same, frequency as the applied frequency. The disclosed recorded medium, modulated by the frequency transfer unit, incorporates a square wave at the applicable frequency and mathematically congruent square waves that are applicable to the target cell(s) pleomorphic life cycle and bandwidth. This applied resonance can either stimulate a cell to a slight higher or lower energy state or destroy the cell if the amplitude (height) and time of application (duration) of the wave are sufficient.

When the disclosed technology is used to destroy a pathogenic cell, the resonance is increased to exceed the molecular bonding capability of the cell, causing the cell to break apart, destroying the organism. As a result of this destruction, the user experiences a local and/or general reaction of the immune system since the body's immune system can now recognize and eliminate the particulate matter resulting from the cells' destruction. Somehow these insidious organisms that cause premature aging and our early demise appear harmless to our immune system until they are exposed to their resonant frequency and are obliterated, thereby enabling the bodies defense mechanism to respond. This immune system response is called a Die Off reaction. The Die Off reaction will continue to occur upon successive treatments until there are no longer enough degenerative cells to stimulate an acute immune response, or until there are no more cells remaining that are sympathetic to the frequencies being applied. Further advantages can be obtained from the disclosed device by periodically screening for a variety of potential degenerative organisms before they have the opportunity to cause harm to the body.

The disclosed system also serves as a screening mechanism for detecting pathogens and other possibly degenerative organisms within the body. In order to screen a body for pathogens, a CD of many known pathogen-destroying frequencies is played using the disclosed frequency transfer system. When the user of the system detects a reaction, the time and location of the reaction is recorded. From this data, the scientific bandwidth that corresponds to a specific pathogen can be determined from known research and records. The reaction can include any number of physical changes or sensations such as pain or inflammation. These reactions, known as a Herxhiemer Reaction, are believed to be the user's body responding to cell destruction and immune system response.

The basis for the destruction of pathogens through frequency modulation is the weak protein bond between molecules, as illustrated in FIGS. 1A–C, with each overlap or intersection region for each protein molecule serving as a weak point. Using this weakness, in combination with increased amplitudes at the pathogen's frequency, even ultra low intensity (10–16 w/m2) standing waves can rupture these bonding regions. When exposed to its most stressful mechanical oscillation mode, the disintegration of a pathogen can be viewed through a microscope. To illustrate why the bonds are disintegrated, FIG. 1A illustrates an example virus capsid 1 using a ten-member protein clumping. In FIG. 1B a mathematical abstraction of the virus capsid 10 is portrayed with a focus on the oscillation of a single protein 2. As can be seen, the focused area is an ellipse having its major axis at the bonding region with the adjacent protein and its minor axis as the center of mass of the protein molecule. An elastic coupling extends along the major axis between the protein molecules. It is at the bonding region between the adjacent protein molecules that the pathogen is weakest. Differential equations, additional information to corroborate the process, as well as specific frequencies, can be found in publications set forth in parent application Ser. No. 09/240,023, and are incorporated herein as though recited in full.

Frequency Transfer System

Figure 2:
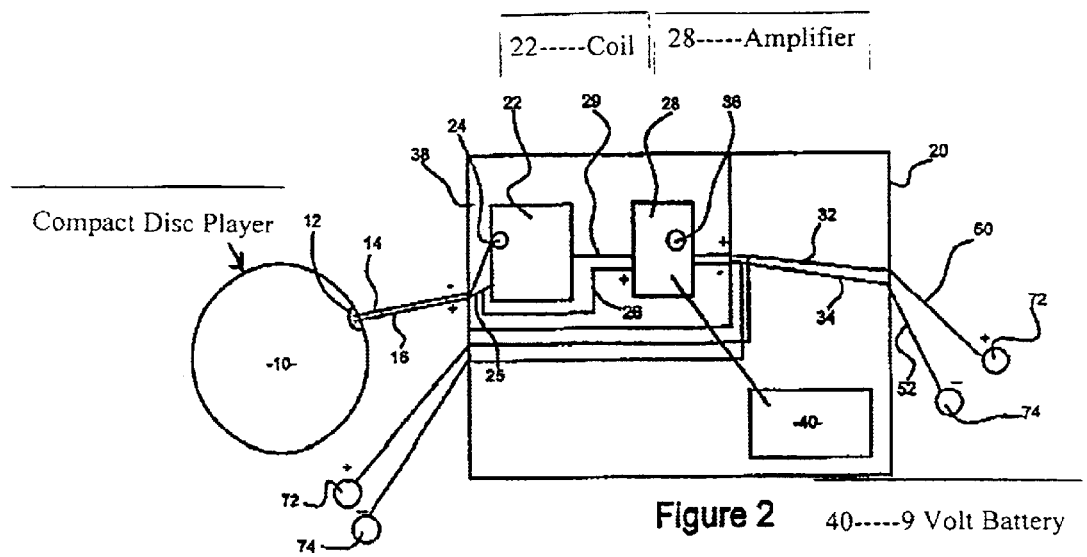
FIG. 2 is a schematic of one method of arranging the interior electronics for the unit.

In the preferred embodiment, the frequency transfer system includes a digital electronic device, such as a CD player, capable of transferring data from a data storage medium, a frequency transfer unit consisting of an amplifier and a coil, and electrode leads having contact surfaces. The system uses only AC current as DC has been proved to be harmful to cellular structures. As shown in FIG. 2, the digital electronic device 10 is preferably a portable CD player, or other equivalent unit, that includes a line-out jack 12 which provides a connection to the frequency transfer unit 20. The voltage output of a portable CD player is only about 0.4 VAC, requiring amplification to achieve any efficacy. This is achieved through the use of an integrated circuit amplifier 28, to increase the output to about 4 to 6 VAC. This low voltage is effective based not on power, but rather on sympathetic resonance and the use of scalar waves.

The connections between the CD player 10 differ from connections used for music in that only one positive 14 and one negative 16 wires are used. The use of three leads, two positive and a negative, as commonly used for stereo, causes phase interference in the coil 22 within the unit 20, eliminating the scalar wave potentials and negating the scalar wave's benefits.

Figure 3:
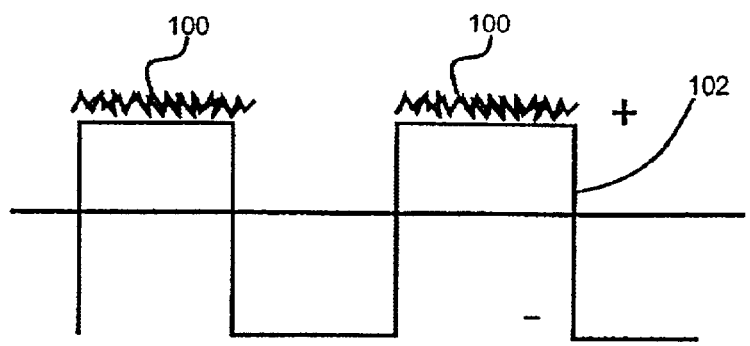
FIG. 3 is a square wave showing the positive and negative location of the current produced by the disclosed device.

A sealed electronics box 38 is contained within the unit 20 to house a coil 22 and amplifier 28 to prevent tampering or damage to the electronics. The coil 22 can be a toroid coil, or the equivalent with primary and secondary windings with a common ground, which will absorb most of the magnetic flux within the core of the coil. The negative lead wire output 14 from the CD player 10 is connected to the ground connection 24 of the coil 22. The positive lead output from the CD player is connected to the input of the coil 22, with a jumper wire lead 26 connected directly to the positive input of an integrated circuit amplifier 28. This creates a phase disparity or bi-phase signal at the output of the integrated circuit amplifier 28 as a result of the current lag within the coil 22 windings. The inductive reactance within the coil 22 results in a one-dimensional electrical, or scalar wave output of the coil which is connected, through lead 29, to the negative input of the integrated circuit amplifier 28. The output leads 32 and 34 of the amplifier are flipped (reversed) to contain most of the scalar potentials 100 at the positive node 102 of the amplifier's output wave(s), as seen in FIG. 3. With a minimum of electrical resistance, due to the exponential harmonic output of the scalar potentials, this configuration enables the disclosed system to be used on more than one person at a time as well as enhance the effectiveness of the applied frequency(s).

The amplifier 28 further contains a potentiometer 36 that is tuned to a mean frequency and predetermined amplitude. This mean frequency is near the center of the bandwidth of applicable therapeutic frequencies. This ensures continuity of signal output for therapeutic applications. Since the electronics box 38 is sealed, the potentiometer 36 cannot be unintentionally altered.

An important and significantly researched aspect of cellular dysfunction is the loss or reversal of cellular polarity. Mutated cells have lost or changed their polarity which prevent adequate communication and bonding with other cells. It is believed that re-establishing proper polarity within the cell(s) can result from the induction of electromagnetic waves when the waves contain scalar potentials and the potentials are most prominent at the positive node of the electromagnetic waves. Another aspect of the aforementioned is an electrostatic attraction, in that it has been observed that mutated cells have displayed a somewhat negative charge. This polar attraction could expedite the capability to induce sympathetic resonance and evisceration of mutated cells. It has also been discovered that scalar waves have a significant impact on the human immune system, enhancing the effectiveness of white blood cells and lymphocytes.

The amplifier 28 is powered by a rechargeable battery 40 to enable the unit to be portable. The recharging of the battery 40, as well as the ability to use direct current to power an amplifier, is well known in the art. Preferably the unit contains low battery indicators, on/off lights and other indicators known in the electronics field.

Optimum results are received when multiple harmonically related congruent square waves are recorded on the CD for simultaneous applications. As stated herein, different pathogens are affected by different frequencies. Recording multiple frequencies, harmonically related, onto the CD will enable the frequencies to work together synergistically, thus eliminating various pathogens and while also targeting the pleomorphic stages of cellular mutation. Once an appropriate frequency has been established for the primary disease, harmonically related frequencies are also established/ recorded within a relevant bandwidth. Longer waves provide more power and are recorded at lower amplitudes as not to override the shorter harmonic wavelengths. The waves must be mathematically congruent, as a lack of congruency will cause phase interference and dissonance. The signal processing of the CD recording, which entails equalization and compression of pathogen specific square waves and their relevant harmonic square waves, determine the overall output of transfer unit.

The amplifier 28 will, as well as increasing the voltage, decrease the rise time of the square waves, thus optimizing the harmonic output of the waves. The interaction of the congruent and incongruent square waves and/or dissonance of the waves are monitored on an oscilloscope during the recording process.

Figure 4:
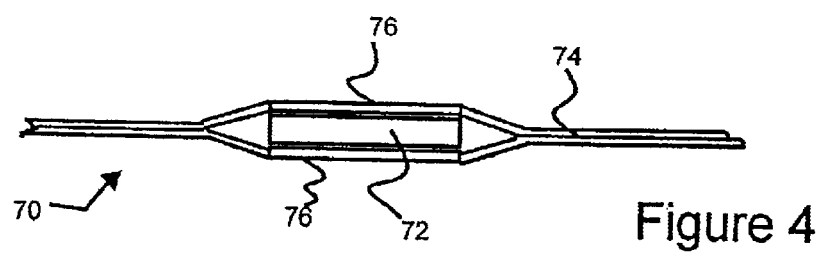
FIG. 4 is a side view of the preferred embodiment for an electrode.

In order to transfer the frequencies to the user, leads 50 and 52 extend from the unit 20 to electrodes 72 and 74 that are place on the body. In the preferred embodiment, illustrated in FIG. 4, the predominately electrical wave electrode 72 is placed within fabric 76 to prevent direct contact with the skin. The fabric 76 can be a continuation of the armband 74 or separate material and the various ways to encase the electrode 72 will be obvious to those skilled in the art. The predominately electromagnetic wave electrode 74 is placed directly onto the skin in conjunction with electrode gel. By preventing both of the electrodes from directly contacting the skin, the user does not feel any of the electrical pulses.

It should be noted that the voltage references herein are within the safe range for humans. This technology can also readily be adapted for animal use and the voltage would necessarily require adjustment in accordance with the physiology of the particular animal.

The desired frequencies are placed onto the recorded modulating medium for a predetermined length of time and may be repeated as necessary to equal the recommended treatment time. The treatment time is dependent upon the pathogen and its severity, user body weight, etc. Since application of the frequencies for periods of time longer than the recommended time period cannot harm the individual, the concern is matter of insuring that the frequencies are used for a period of time sufficient to allow destruction of the pathogens' molecular bonds. As stated herein, the frequencies are not of an amplitude or amperage as to disrupt or harm healthy cells. Only the pathogens residing at the outer portion of the tissues are destroyed by the frequencies with pathogens residing within the tissue migrating outward to occupy the empty spaces. The use of repeated treatments destroys pathogens as they migrate to the outer portions of the tissues until all pathogens have been destroyed.

As each frequency is aligned with the frequency of the pathogenic protein bond to be broken, only bonds that are affected by these frequencies are those specific targeted pathogens. Normal cells are prevented from being affected by the recorded frequencies by their inherent structure. A normal cell has a hexagonal and pentagonal periphery, a stronger molecular matrix, and a substantially higher mortal oscillation rate. The voltage required to affect a normal cell is in the range of 50 volts or 1 ampere and the safeguards provided in the disclosed device prevent the voltage level from reaching even close to a harmful point.

Since other modifications and changes varied to fit particular operating requirements and environments will be apparent to those skilled in the art, the invention is not considered limited to the example chosen for the purposes of disclosure, and covers all changes and modifications which do not constitute departures from the true spirit and scope of this invention.

What is claimed is:

1. A frequency transfer system comprising:
    a digital electronic device having at least one line out jack and being capable of transferring electromagnetic waves from a data storage medium, said data storage medium being recorded with at least one square wave at a predetermined frequency;
    a transfer unit, said transfer unit having no transformer and receiving said line out jack and having:
    a coil, said coil receiving said square waves, absorbing magnetic flux from said electromagnetic square waves and having an output of scalar square waves;
    an amplifier having a positive input and a negative input and a positive output and a negative output, said amplifier increasing voltage and reversing wave polarities between said positive input and said negative input and said positive output and said negative output;
    an incoming positive lead from said digital electronic device, said incoming positive lead having a first portion and a second portion, said first portion being connected to said coil and said second portion being connected to said amplifier;
    an incoming negative lead from said digital electronic device, said incoming negative lead being connected to a ground on said coil;
    a transfer lead, said transfer lead connecting said scalar waves from said coil to said amplifier; and
    a rechargeable battery, said rechargeable battery powering said amplifier;
    wherein, electromagnetic square waves from said digital electronic device are received by said transfer unit and are converted to predominately scalar output square waves having an increased voltage and reversed polarity within said transfer unit thereby placing the greatest scalar potentials at the positive node of said output square wave.

2. The frequency transfer system of claim 1, wherein said digital electronic device is a CD player and wherein said data storage medium is a CD.

3. The frequency transfer system of claim 2, wherein said CD player is a hand-held unit.

4. The frequency transfer system of claim 1, wherein said amplifier further comprises a potentiometer, said potentiometer being set at a mean level to maintain output from said amplifier in an optimum square wave amplitude for therapeutic applications.

5. The frequency transfer system of claim 1, wherein said data storage medium is recorded with at least one square wave frequency for transmission to said transfer unit.

6. The frequency transfer system of claim 5, wherein at least one of said at least one square wave frequency is a pathogen destroying square wave frequency.

7. The frequency transfer system of claim 6, wherein each of said at least one square wave frequency is congruent to other square wave frequencies being transmitted simultaneously.

8. The transfer system of claim 1 wherein said square wave frequencies are created on a frequency counter/generator, said frequencies being stored on said data storage medium.

9. The frequency transfer system of claim 1 wherein said coil is a toroid coil.

10. The frequency transfer system of claim 9, wherein said coil is copper.

11. The transfer system of claim 1 further comprising at least one pair electrodes having body-affixing means, each of said at least one pair of body affixing means affixing said electrodes to a user's body.

12. The transfer system of claim 11 wherein a first of said pair of electrodes contacts said user's skin and a second of said electrodes is proximate said user's skin.

13. The transfer system of claim 12 wherein said electrode is secured within said body affixing means to prevent contact with said user's skin.

14. The transfer system of claim 11 wherein said electrode surface is stainless steel.

15. The transfer system of claim 1 wherein waves passing through said second section enter said amplifier prior to waves passing through said coil, thereby creating a phase disparity in said transfer unit output.

16. A method of screening a body for pathogens comprising:
   preparing a data storage medium containing at least one square wave frequency for transmission synchronously with at least one mathematically congruent square wave of said at least one square wave frequency, wherein each of said at least one square wave frequency corresponds to a particular pathogen-destroying frequency, and wherein the timing of each of said at least one square wave frequency on said data storage medium is known;
   transmitting said at least one square wave through a frequency transferring device to said body, said frequency transferring device comprising:
      a coil, said coil absorbing magnetic flux from said square waves and having an output of scalar waves;
      an amplifier, said amplifier having a positive input and a negative input and a positive output and a negative output, and increasing voltage and reversing wave polarities between said positive input and said negative input and said positive output and said negative output;
      an incoming positive lead from said digital electronic device, said incoming positive lead having a first portion and a second portion, said first portion being connected to said coil positive input and said second portion being connected to said amplifier positive input;
      an incoming negative lead from said digital electronic device, said incoming negative lead being connect to a ground on said coil;
      a transfer lead, said transfer lead connecting said scalar waves from said coil to said amplifier;
   at least one pair of electrodes, said electrodes being connected to said transfer unit by output leads;
   modulating said at least one square wave frequency and said at least one harmonic from said data storage medium to each of said electrode, wherein, said at least one square wave frequency and said at least one harmonic enters said body via one of said electrode;
   recording times and locations of bodily reactions to said at least one wave and at least one harmonic; and
   analyzing said time and location of bodily reactions to determine the correspondence between said reactions and said known pathogen-destroying frequencies;
   wherein, said correspondence indicates presence of a specific pathogen in said body.

17. A method of destroying pathogens comprising:
   preparing a data storage medium containing at least one square wave frequency for transmission synchronously with at least one harmonic of said at least one square wave frequency, wherein each of said at least one square wave frequency corresponds to a particular pathogen-destroying frequency, and wherein the timing of each of said at least one square wave frequency on said data storage medium is known;
   affixing a frequency transferring device to a body, said frequency transferring device comprising:
      a coil, said coil absorbing magnetic flux from said electromagnetic waves and having an output of scalar waves;
      an amplifier having a positive input and a negative input and a positive output and a negative output, said amplifier increasing voltage and reversing wave polarities between said positive input and said negative input and said positive output and said negative output;
      an incoming positive lead from said digital electronic device, said incoming positive lead having a first portion and a second portion, said first portion being connected to said coil and said second portion being connected to said amplifier,
      an incoming negative lead from said digital electronic device, said incoming negative lead being connect to a ground on said coil;
      a transfer lead, said transfer lead connecting a combined current from said coil to said amplifier;
   transmitting said at least one square wave frequency and said at least one harmonic to each of said contact surfaces, wherein, said at least one square wave frequency and said at least one harmonic enters said body via said electrodes;
   transmitting said square waves for a predetermined length of time based on a predetermined schedule,
   wherein said at least one square wave frequency increases the vibrational frequency of said pathogens to break cellular bonds within said pathogen.

* * * * *